United States Patent [19]
Heaven et al.

[11] Patent Number: 5,344,397
[45] Date of Patent: Sep. 6, 1994

[54] CHOLANGIOGRAM CATHETER

[75] Inventors: Malcolm D. Heaven, Hopewell, N.J.; Hira V. Thapliyal, Mountain View, Calif.

[73] Assignee: Advanced Surgical, Inc., Princeton, N.J.

[21] Appl. No.: 903,587

[22] Filed: Jun. 26, 1992

[51] Int. Cl.$^5$ .............................................. A61M 37/00
[52] U.S. Cl. ........................................ 604/95; 604/96; 604/282; 606/192
[58] Field of Search ................... 604/95–100, 604/214, 216, 280, 282; 606/192, 194, 197

[56] References Cited

U.S. PATENT DOCUMENTS

| | | | |
|---|---|---|---|
| 1,763,079 | 6/1930 | Zacsek | 604/97 |
| 2,950,717 | 8/1960 | Bouet | 604/214 |
| 3,154,078 | 10/1964 | Goodrich, Sr. | 604/97 |
| 3,211,151 | 10/1965 | Foderick et al. | 604/97 |
| 3,572,552 | 3/1971 | Guinn | 604/214 |
| 3,605,725 | 9/1971 | Bentov | 604/95 |
| 3,978,863 | 9/1976 | Fettel et al. | 604/100 |
| 4,233,983 | 11/1980 | Rocco | 604/97 |
| 4,245,639 | 1/1981 | La Rosa | 604/97 |
| 4,444,188 | 4/1984 | Bazell et al. | 604/95 |
| 4,586,923 | 5/1986 | Gould et al. | 604/95 |
| 4,758,221 | 7/1988 | Jureidini | 604/98 |
| 4,960,410 | 10/1990 | Pinchuk | 604/96 |
| 4,976,688 | 12/1990 | Rosenblum | 604/95 |
| 5,024,655 | 6/1991 | Freeman et al. | 604/96 |
| 5,057,078 | 10/1991 | Foote et al. | 604/98 |
| 5,125,895 | 6/1992 | Buchbinder et al. | 604/95 |

FOREIGN PATENT DOCUMENTS 9111213  8/1991  World Int. Prop. O. ............ 604/95

Primary Examiner—C. Fred Rosenbaum
Assistant Examiner—Mark Bockelman
Attorney, Agent, or Firm—Stephen F. K. Yee

[57] ABSTRACT

A balloon catheter including a pumping mechanism for inflating the balloon, an actuator and control wire for deflecting a distal tip of the catheter and a luer connection for passing a guidewire through the catheter. The balloon can be inflated with a push button which can be locked when depressed so as to inflate the balloon. The balloon is deflated by rotating the push button so that a return spring expands an air bladder and returns the push button to a non-inflating position. The control wire is manipulated by a pivotal lever or a slidable ring. The ring can include a projection which extends through a slot in the housing or the ring can include a circumferentially extending surface which can be finger actuated at any position around the catheter tube.

29 Claims, 5 Drawing Sheets

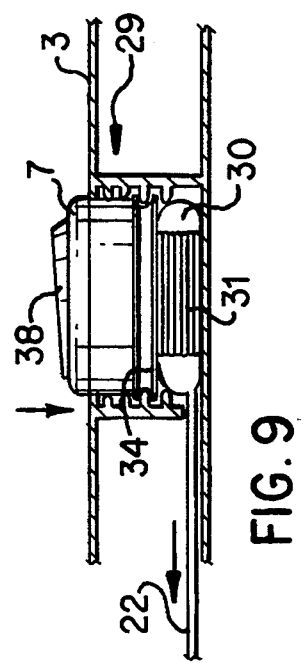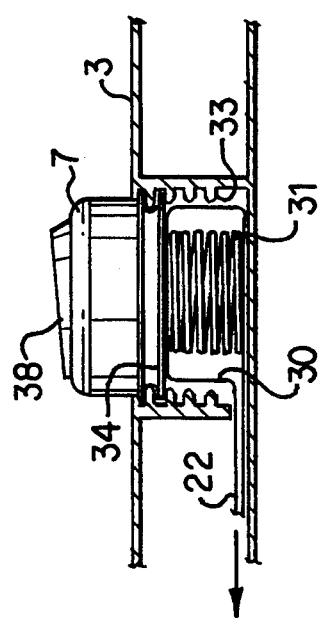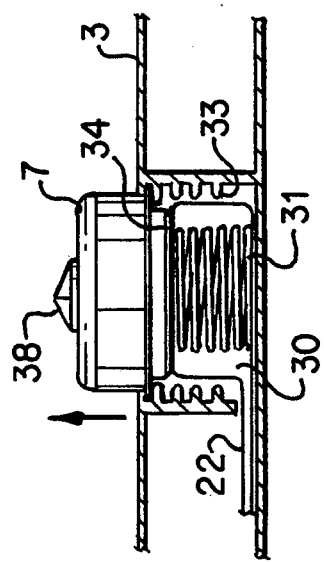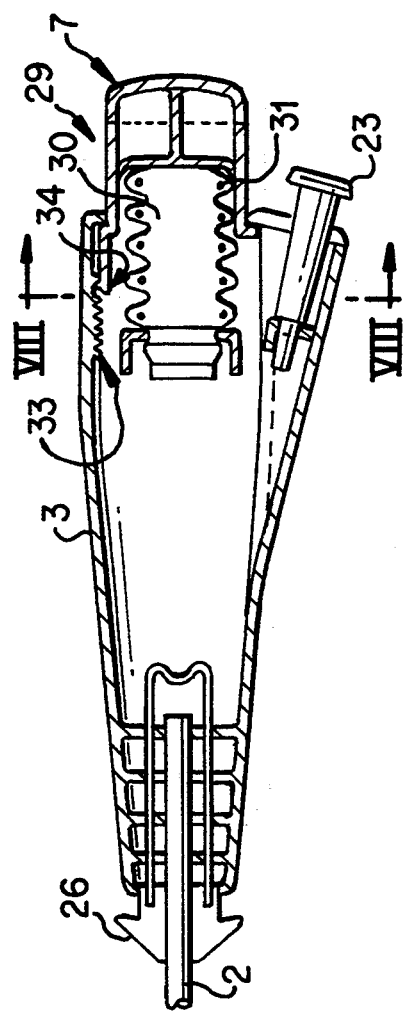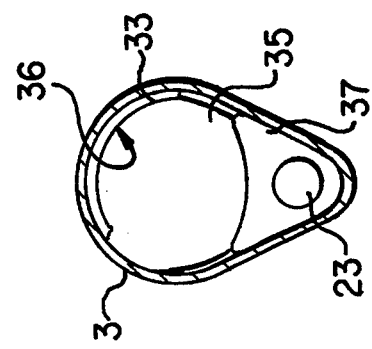

CHOLANGIOGRAM CATHETER

FIELD OF THE INVENTION

This invention relates to a new and improved catheter design, useful in the field of laparoscopic cholecystectomy.

BACKGROUND OF THE INVENTION

In order to perform laparoscopic cholecystectomy safely and effectively, it is necessary for the surgeon to completely visualize the biliary tree. This is accomplished using, for example, a cholecystocholangiogram, in which a radio-opaque dye is injected into the cystic duct and the biliary tree anatomy is recorded via, for example, a cinefluorocholangiographic unit. In order to carry this out, a catheter must be inserted into the cystic duct to allow injection of the contrast fluid. Existing catheters do not optimize the ergonomics in such a way as to improve the speed and efficiency of the entire procedure significantly.

A major problem in carrying out successful cholangiographs is the safe introduction of the cholangiogram catheter into the duct. Additionally, there are frequently problems associated with maintaining the correct location of the catheter during the actual operation of the fluoroscope, during which time the operating staff leave the immediate vicinity of the patient. There are also dangers associated with inserting a relatively rigid and fixed geometry device into the duct, as at this initial state, the anatomy is not known. Neither is it known what obstructions might be present.

A device marketed by International Medical American Catheter has a fixed, rigid curvature at the end, which does not lend itself to atraumatic insertion into the duct, plus it has no means for locking it in position. A device marketed by Arrow Karlan also has a fixed curved end, but does incorporate a distal balloon to aid with retention during the actual fluoroscope operation. However, the device still has severe limitations. Other devices also have numerous deficiencies.

SUMMARY OF THE INVENTION

The invention provides a balloon catheter comprising a housing, a catheter tube extending from the housing, an inflatable balloon at a distal end of the catheter tube and a fluid passageway extending between the balloon and the housing. The fluid passageway allows inflation of the balloon when pressure is applied to a fluid medium in the fluid passageway. An inflation device supported within the housing is in fluid communication with the fluid passageway and is manually operable to pressurize a fluid medium in the fluid passageway for inflation of the balloon.

The inflation device can include a bladder in fluid communication with the fluid passageway, the bladder being biased in an expanded condition, and a button movable between first and second positions. The bladder can be compressed when the button is moved from the first position to the second position whereby the balloon is expanded due to pressurizing a fluid medium in the fluid passageway. The bladder can be biased by a return spring and/or resilient material of the bladder.

The balloon catheter can include an articulating means for bending the distal end of the catheter tube. The articulating means can include a control wire extending between the distal end of the catheter tube and an actuator supported by the handle, the actuator being movable between first and second positions. The distal end of the catheter tube can be deflected when the actuator is moved from the first to the second position. The articulating means can include a control wire lumen surrounding the control wire.

The balloon catheter can include a guidewire/contrast medium lumen for passing a guidewire and/or contrast medium through the catheter. The guidewire lumen extends through the distal end of the catheter body and through the handle. The guidewire lumen and the control wire lumen can be lumens of a bifilar tube or lumens of separate tubes.

The control wire can include an integral loop formed at a distal end thereof, the loop being adhesively bonded to the tip of the catheter body such that the loop surrounds the guidewire. The distal end of the catheter can include a metal tube such as a small diameter stainless steel tube, a plastic tube surrounding the metal tube with a distal portion of the plastic tube extending beyond a distal end of the metal tube. A helical spring can surround the plastic tube. The balloon can be supported on the distal portion of the plastic tube.

The button can be mounted on a surface of the handle extending in a direction parallel or perpendicular to the catheter tube. The housing can be cylindrical in shape and the button can be mounted in a proximal end surface of the housing. The button is preferably rotatable from a first angular orientation to a second angular orientation such that the button is lockable in the second position when the button is in the first angular orientation and the button is free to return to the first position when the button is in the second angular orientation. The button can include at least one locking projection thereon and the housing can include one or more locking teeth, the locking projection engaging one of the locking teeth when the button is in the second position and in the first angular orientation. The button can include a position indicator for identifying when the button is in the first or second angular orientation.

The control wire can comprise a lever pivotally mounted on the housing or a member which is slidably mounted on the housing. The member can include a finger actuated projection thereon. The member can comprise a ring coaxial with the catheter tube and having an annular surface which can be finger actuated at any position around the catheter tube. The ring can be located at a distal end of the handle.

DESCRIPTION OF THE DRAWINGS

FIG. 7 shows a cross section of a housing of a catheter in accordance with another embodiment of the invention;

FIG. 8 shows a cross section taken along the line VIII—VIII in FIG. 7;

FIG. 9 shows details of an inflation device in accordance with the invention wherein the push button is in a position at which the balloon is inflated;

FIG. 10 shows the push button of FIG. 9 but in a position at which the balloon is not inflated;

FIG. 11 shows the push button of FIGS. 9 and 10 but in a position at which the button will not engage locking teeth in the housing;

DETAILED DESCRIPTION OF THE PREFERRED EMBODIMENTS

The catheter of the present invention is described with reference to FIGS. 1–16.

The device proposed in this invention can incorporate the following features such as a guidewire/contrast medium lumen to accommodate a standard guidewire and/or injection of a contrast solution, an atraumatic soft distal tip to allow gentle engagement of the duct, and/or an articulateable tip to aid entry where there is significant tortuosity, the catheter being curved at will, thus adding a significant degree of steerability to the device.

In order to hold the device safely in position in the duct during the cholecystocholangiogram, the device is equipped with a distal balloon. The balloon can be inflated to the appropriate size using a built-in pump inflation device which is of advanced ergonomic design mounted conveniently in the handle of the device. This feature in particular simplifies the procedure significantly, and the catheter as a whole allows one-handed operation.

Figure 1:
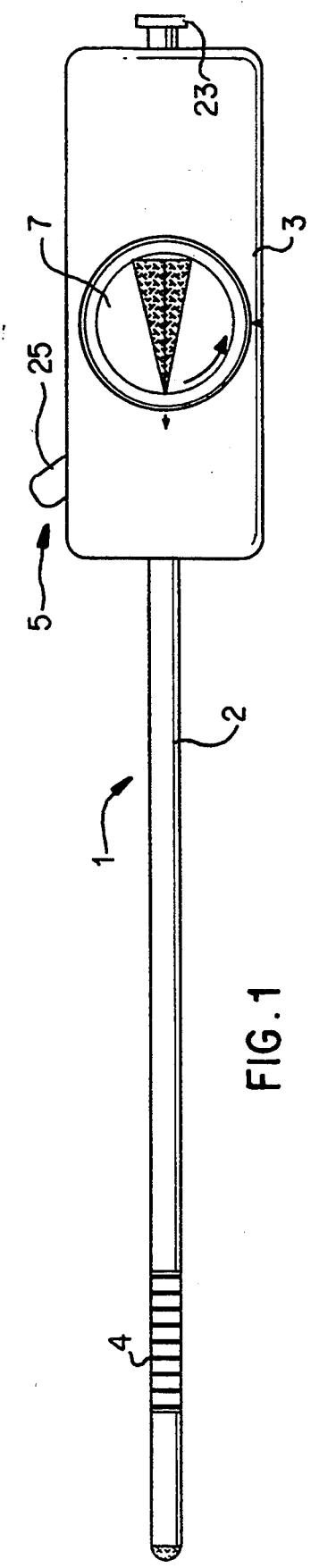
FIG. 1 shows a balloon catheter in accordance with one embodiment of the invention.
Figure 2:
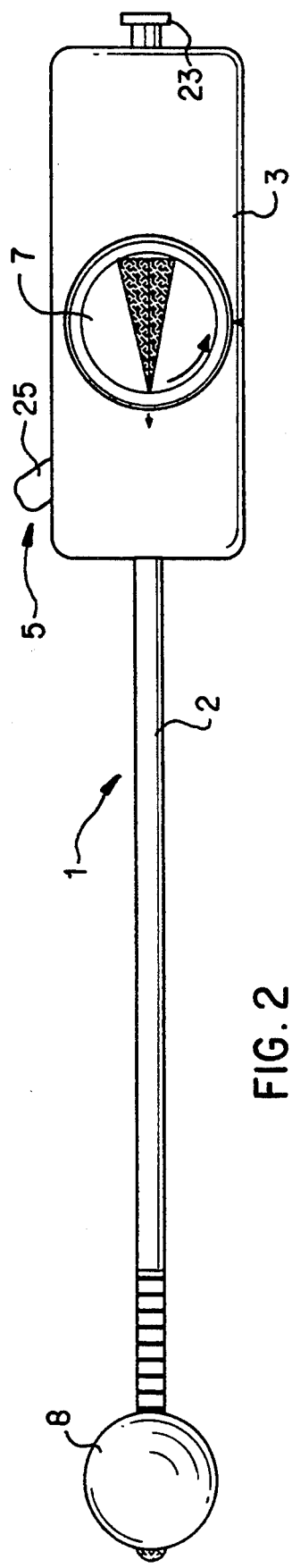
FIG. 2 shows the catheter of FIG. 1 with the balloon in the inflated condition.
Figure 3:
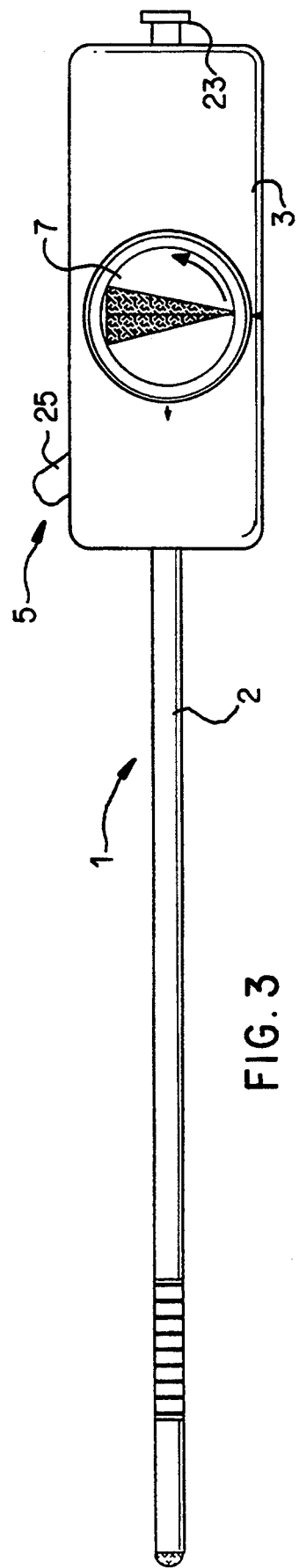
FIG. 3 shows the catheter of FIG. 1 with the push button for inflating the balloon in a position at which the balloon is deflated.

The catheter 1 in accordance with a preferred embodiment of the invention includes a main tube 2 extending between a handle 3 and an articulateable tip 4 as shown in FIGS. 1–3. The main tube 2 is a straight tube in the illustrated embodiment for purposes of introducing the catheter through a trocar. However, the main tube can have other shapes such as a prebent shape with or without an articulateable tip. The handle 3 includes a manually moved actuator 5 attached to a control/steering wire 6, as shown in FIG. 4, and a manually repressible button 7 for inflating a balloon 8 which surrounds a distal portion of the articulateable tip 4.

Figure 4:
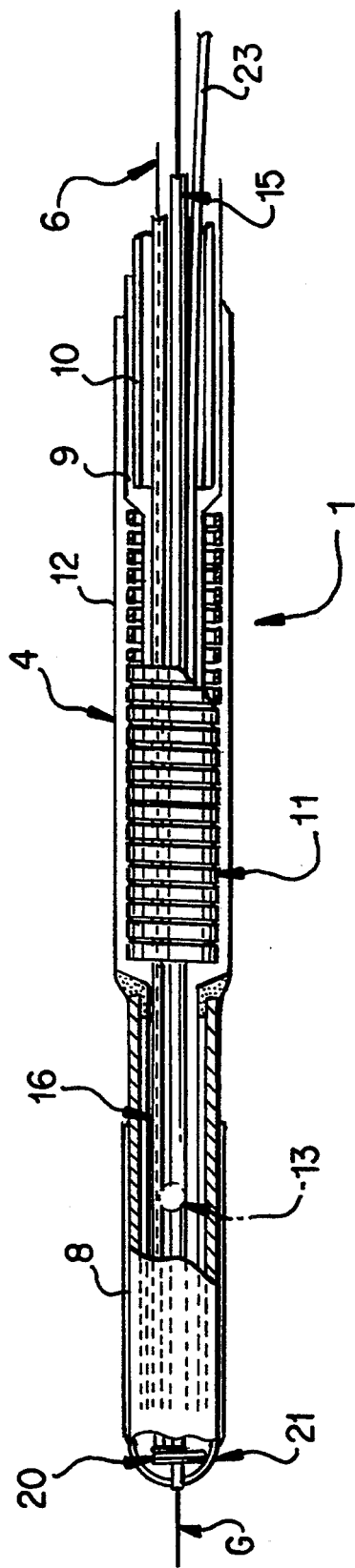
FIG. 4 shows an articulateable tip of the catheter of FIG. 1.

The articulateable tip 4 can be made by heat shrinking a plastic tube 9 over a stainless steel metal tube 10 having a suitable length such as about 3 inches and a suitable diameter such as about 40 mils, as shown in FIG. 4. Alternatively, the tube 10 can be of a plastic or nonmetal material having sufficient strength and rigidity. The heat-shrinkable plastic 9 can comprise any suitable material such as polyvinylidene fluoride, e.g., Kynar manufactured by Pennwalt Corp. The plastic tube 9 should extend beyond the distal end of the metal tube 10. For example, tube 9 can have any suitable length, e.g., about 4 inches and any suitable wall thickness, e.g., about 3 mils. A helical spring 11 having a suitable length such as about 1 inch is placed tightly around the plastic tube 9 such that a proximal end of the spring faces a distal end of the metal tube 10 and a portion such as about 0.3 inch of the distal end of the plastic tube 9 is not covered by the spring 11. The spring 11 is covered by another heat-shrinkable plastic tube 12 which stops short of the balloon 8. An inflation hole 13 is provided through the uncovered portion of the plastic tube 9. The inflation balloon 8 can have a suitable length such as about 0.3 inch and a suitable maximum inflation size such as about 7 min. The balloon 8 is attached over the uncovered portion of the plastic tube 9 such that the inflation hole 13 is in fluid communication with the interior of the balloon 8. The plastic tube 9 is cut flush with the distal end of the balloon 8.

Figure 5:
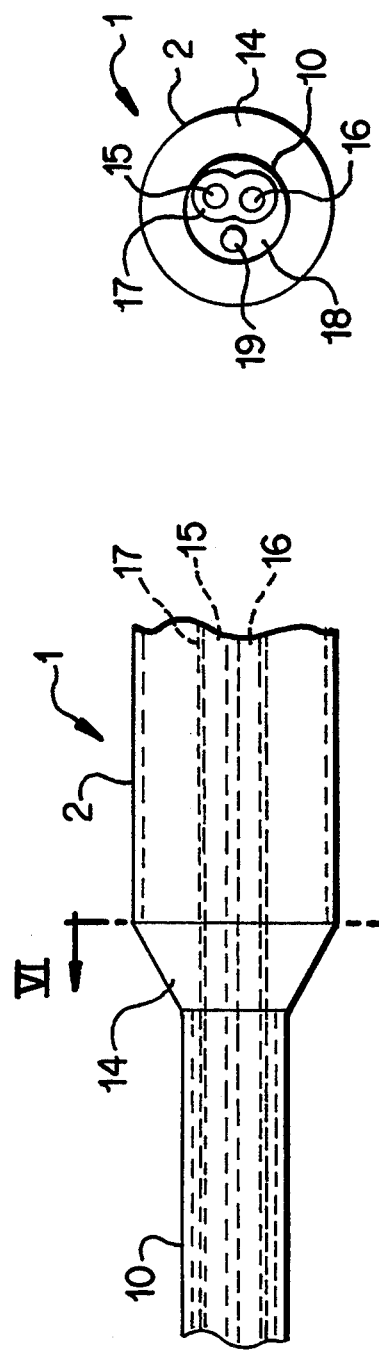
FIG. 5 shows a connection between a main tube and the articulateable tip of a catheter in accordance with the invention.

A stainless steel manifold 14 in the form of a tapered sleeve connects the 40 mil O.D. articulateable tip 4 to the main tube 2, as shown in FIG. 5. The main tube 2 comprises a stainless steel tube having a suitable length such as about 7 inches and a suitable outside diameter such as about 120 mils. The metal tube 10 is attached to the manifold 14 by any suitable means such as a mechanical connection, a metallurgical bond and/or adhesive. For instance, the proximal end of the metal tube 10 can be flared radially outwardly so as to engage a flange inside the manifold 14 and adhesive can also be provided between the metal tube 10 and the manifold 14. Likewise, the main tube 2 can be attached to the manifold 14 by any suitable means.

Figure 6:
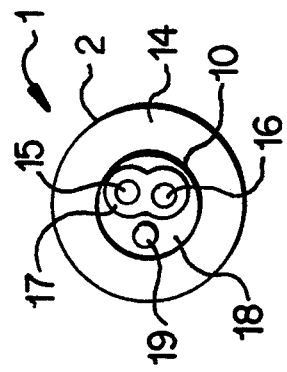
FIG. 6 shows a cross section taken along the line VI-VI in FIG. 5.

It may be desirable to provide suitable means such as lumens 15, 16 in the metal tube 10 for receiving a guidewire/contrast medium, a control/steering wire for inflation of the balloon. In the case of a 40 mil O.D. metal tube 10, it may be possible to fix only two guide tubes in the metal tube 10. Such tubes can be separate tubes or a bifilar tube can be used to provide two lumens 15, 16 wherein one lumen 15 thereof receives the guidewire/contrast medium and the other lumen 16 receives the control wire 6. The bifilar tube 17 can be bonded at the proximal end of the metal tube 10 such that an inflation passage 19 in communication with the interior of the balloon remains in the metal tube 10, as shown in FIG. 6. For instance, the bifilar tube can be adhesively bonded to the manifold 14 while maintaining a mandrel extending into the metal tube 10. After curing/setting of the adhesive 18, the mandrel can be removed to provide the inflation passage 19 for the balloon extending through the manifold 14.

The control wire 6 can comprise a suitable wire such as 8 mil stainless steel wire. The wire can be looped at one end and the loop/coil 20 can be soldered, if desired, to maintain its shape, as shown in FIG. 4. The loop/coil 20 is bent 90° such that the coils are perpendicular to the rest of the wire 6. The wire 6 is inserted into one of the lumens 15, 16 of the bifilar tube 17 and the loop/coil 20 is attached to the end of the bifilar tube 17 such that it does not block the lumen 15 for the guidewire/contrast solution. For instance, the bifilar tube can be cut such that the portion of the bifilar tube 17 forming the lumen 16 for the control wire is shorter than the portion of the bifilar tube 17 forming the lumen 15 for the guidewire and the loop/coil 20 can surround the periphery of the portion of the bifilar tube 17 forming the guidewire lumen 15. To provide an atraumatic tip, adhesive 21 in the shape of a rounded tip can be used to attach the coil/loop 20 and the bifilar tube 17 to the distal end of the plastic tube 9, as shown in FIG. 4. A balloon extension tube 22 can also be bonded to the manifold 14 to provide a balloon inflation passage which extends to the handle 3, as shown in FIGS. 9–11.

The handle 3 can be provided in two parts which are attached together by suitable means such as screws, snap fittings and/or adhesive. The proximal end of the main tube 2 can be attached to the handle by any suitable means such as a mechanical, metallurgical and/or adhesive connection. The bifilar tube 17 and the balloon extension tube 22 extend into the handle 3 and a suitable luer connection 23 can be attached to the lumen 15 for the guidewire/contrast medium, as shown in FIGS. 1–3, 7, 8 and 12–16.

Figure 12:
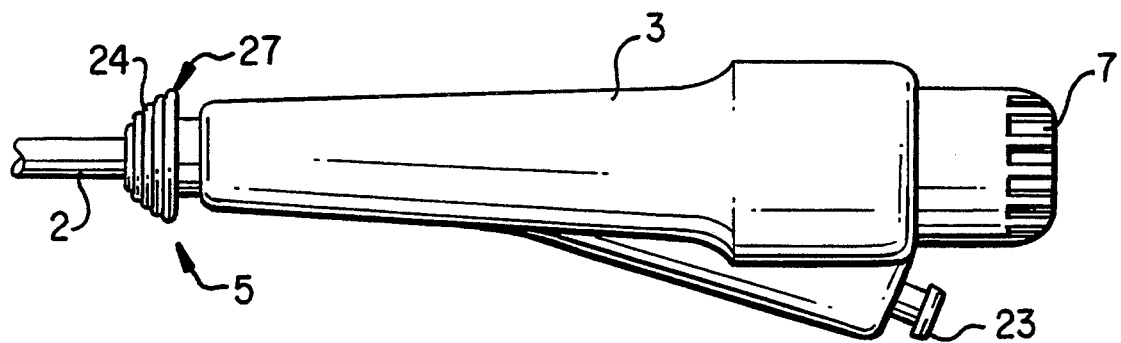
FIGS. 12–16 show various configurations of a housing in accordance with the invention as well as various configurations of an actuator for a control wire.
Figure 13:
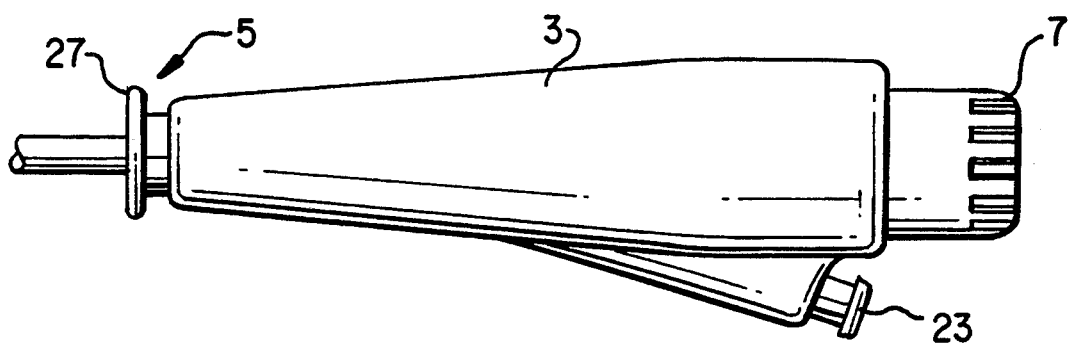
Figure 14:
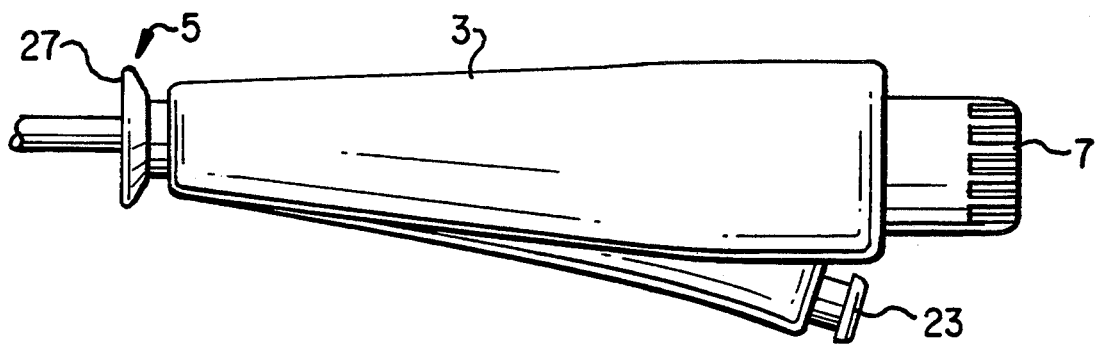
Figure 15:
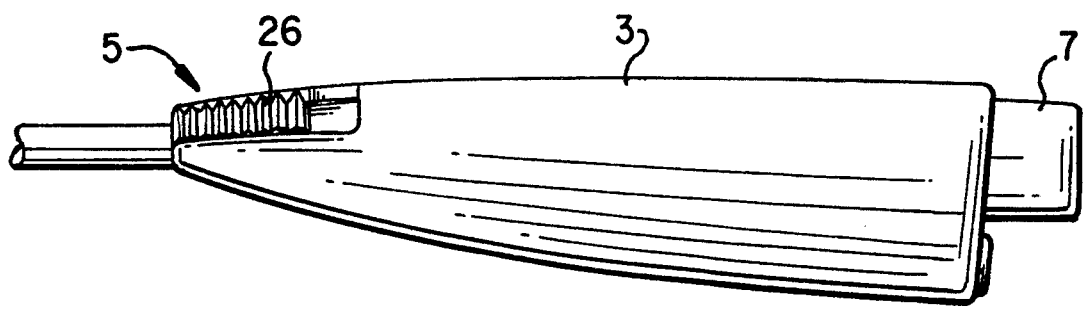
Figure 16:
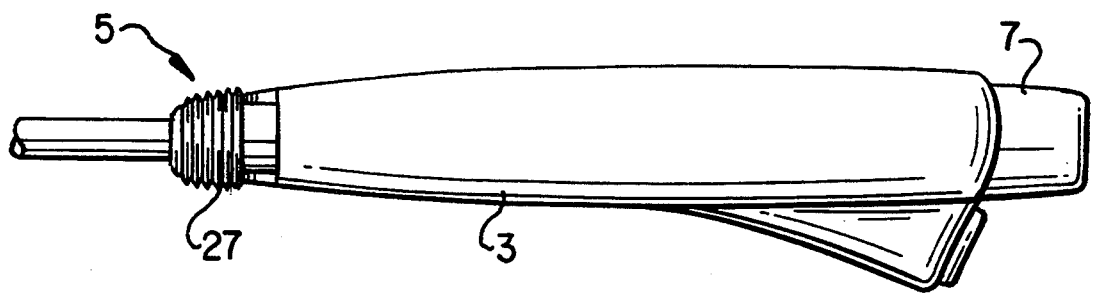

The handle 3 includes an actuator 5 for the control wire 6. For instance, the actuator can comprise a pivotable lever 25 (FIGS. 1–3) or an axially slidable member such as a projection 26 or frusto-conically shaped ring 27. The ring can include the projection 26, as shown in FIG. 15, or the ring can include an annular surface 24 coaxial with main tube 2 so as to allow 360° actuation of the control wire 6, as shown in FIG. 12. The control wire 6 can be crimped, welded, bonded or otherwise attached to the actuator 24 such that movement of the actuator 24 bends the distal end of the articulateable tip 4. The projection 26 and lever 25 can be provided on the side of the handle 3 towards which the tip 4 bends when the control wire 6 is pulled by the actuator 5. In the case of the ring actuator 27, the handle 3 can include a visual indicator such as a projection on the housing to show the direction in which the tip 4 is bent.

The handle 3 also includes an inflation mechanism 29 for inflating the balloon 8, as shown in FIGS. 7 and 9–11. In particular, the balloon extension tube 22 is attached to an air bladder 30 which is spring-biased in an expanded condition by means of return spring 31. Alternatively, other types of springs can be used or the spring 31 can be omitted in the case where the bladder material is resilient enough to return to the expanded condition on its own. A manually repressible push-button 32 is mounted on the handle 3 such that the button 32 can be depressed in steps to incrementally fill up the balloon 8. The handle 3 can include locking teeth 33, and the button 32 can include locking projections 34 which engage the teeth 33, as shown in FIGS. 7–11. The button 32 can be rotatable such that the return spring 31 will expand the air bladder 30 and return the button 32 along a guide track 35 to its initial position at which the balloon 8 is deflated. The handle 3 can also include a rotation stop 36 which engages a rotation stop 37 on the button 32 to allow easier positioning of the button 32 when it is desired to deflate the balloon 8. The button 32 can include a position indicator 38 to identify whether the button 32 is aligned in a position for filling the balloon 8 or a position for deflating the balloon.

FIGS. 12–16 show various cylindrical configurations for the housing 2 and the actuator 5. In addition, the actuator 5 can be a slidable member having a projection 26 extending through a slot in the housing or a ring 27 having an annular surface 24 for 360° actuation. The control wire 6 can be moved by single finger actuation, such as by a user's thumb, by moving the actuator 5 towards the button 7.

It is, of course, possible to embody the invention in specific forms other than those described above without departing from the spirit of the present invention. The embodiments described above are merely illustrative and should not be considered restrictive in any way. The scope of the invention is given in the appended claims, rather than the preceding description, and all variations and equivalents which fall within the range of the claims are intended to be embraced therein.

What is claimed is:

1. A balloon catheter comprising;
   a housing;
   a catheter tube extending from the housing and having a bendable distal end portion;
   an inflatable balloon at a distal end of the catheter tube;
   control means for controllably bending the distal end portion of the catheter tube, the control means including an actuator supported by the housing and coupling means connecting the actuator and said distal end portion;
   a first lumen extending through the housing, through the catheter body and through the distal end of the catheter body, said first lumen providing a passage through the catheter body for a guidewire or a contrast fluid;
   a fluid passage extending between the balloon and the housing, the fluid passageway allowing inflation of the balloon when pressure is applied to a fluid medium in the fluid passageway; and
   an inflation device built-in and supported within the housing, the inflation device being in fluid communication with the fluid passageway and having manually operable means supported by the housing to pressurize a fluid medium in the fluid passageway for inflation of the balloon.

2. The balloon catheter of claim 1, wherein the inflation device includes a bladder in fluid communication with the fluid passageway, the bladder being biased in an expanded condition, and the manually operable means includes a button movable between first and second positions, the bladder being compressed when the button is moved from the first to the second position to expand the balloon by pressurizing the fluid medium in the fluid passageway.

3. The balloon catheter of claim 2, further comprising a spring biasing the bladder in the expanded condition.

4. The balloon catheter of claim 2, wherein the button is mounted at a position between opposite ends of the housing;

5. The balloon catheter of claim 2, wherein the button is mounted at an end of the housing.

6. The balloon catheter of claim 2, wherein the housing is elongated in shape and the button is mounted in a proximal end surface of the housing.

7. The balloon catheter of claim 2, wherein the button is rotatable from a first angular orientation to a second angular orientation, the button being lockable in the second position when the button is in the first angular orientation and the button being free to return to the first position when the button is in the second angular orientation.

8. The balloon catheter of claim 7, wherein the button includes at least one locking projection thereon and the housing including one or more locking teeth, the locking projection engaging one of the locking teeth when the button is in the second position and in the first angular orientation.

9. The balloon catheter of claim 7, wherein the button includes a position indicator for identifying when the button is in the first or second angular orientation.

10. The balloon catheter of claim 1, wherein the control means includes a control wire extending between the distal end of the catheter tube and the actuator supported by the housing, the actuator being movable between first and second positions, the distal end portion of the catheter tube being deflected when the actuator is moved from the first to the second position.

11. The balloon catheter of claim 10, wherein the actuator comprises a lever pivotally mounted on the housing.

12. The balloon catheter of claim 10, wherein the actuator comprises a member which is slidably mounted on the housing.

13. The balloon catheter of claim 12, wherein the member includes a finger actuated projection thereon.

14. The balloon catheter of claim 12, wherein the member comprises a ring coaxial with the catheter tube and having an annular surface which can be finger actuated at any position around the catheter tube.

15. The balloon catheter of claim 14, wherein the ring is located at a distal end of the housing.

16. The balloon catheter of claim 5, further comprising a second lumen extending from the housing and through the catheter body, the control wire passing through the second lumen.

17. The balloon catheter of claim 16, wherein the first and the second lumen are lumens of a bifilar tube.

18. The balloon catheter of claim 16, wherein the first and the second lumen are lumens of separate tubes.

19. The balloon catheter of claim 5, wherein the control wire includes an integral loop formed at a distal end thereof, the loop being adhesively bonded to the tip of the catheter body such that the loop surrounds the guidewire lumen.

20. The balloon catheter of claim 1, wherein the distal end of the catheter includes a metal tube, a plastic tube surrounding the metal tube with a distal portion of the plastic tube extending beyond a distal end of the metal tube, and a helical spring surrounding the plastic tube with a proximal end of the helical spring positioned adjacent the distal end of the metal tube.

21. The balloon catheter of claim 20, wherein the balloon is supported on the distal portion of the plastic tube with a proximal end of the balloon positioned adjacent distal end of the spring.

22. The balloon catheter of claim 1, further comprising a second lumen extending from the housing and through the catheter body and through the distal end of the catheter body, said coupling means passing through the second lumen.

23. A balloon catheter comprising:
a catheter tube having a bendable distal end portion;
an inflatable balloon at the distal end of the catheter tube;
a housing providing a handle on the proximal end of the catheter tube;
a fluid passageway extending between the balloon and the handle housing;
articulation means supported on the handle housing for bending the distal end portion of the catheter tube, the articulation means including an actuator supported by the housing and coupling means connecting the actuator and said distal end portion;
a first lumen extending through the handle housing, through the catheter body and through the distal end of the catheter body, said first lumen providing a passage through the catheter body for a guidewire or contrast fluid; and
an inflation device supported within the handle housing to pressurize a fluid medium in the fluid passageway for inflation of the balloon, the inflation device having a resilient distendable fluid container in fluid communication with the fluid passageway and manually operable means supported by the housing to apply pressure to the fluid container to pressurize the fluid medium.

24. The balloon catheter of claim 23, wherein the inflation device includes a resilient means to bias the fluid container in the distended condition, and the manually operable means includes an element displaceable between first and second positions, the fluid container being pressed when the element is moved from the first to the second position to pressurize the fluid medium in the fluid passageway.

25. The balloon catheter of claim 24, wherein the displaceable element is rotatable from a first angular orientation to a second angular orientation, the element being lockable in the second position when the element is in the first angular orientation and the element being free to return to the first position when the element is in the second angular position.

26. The balloon catheter of claim 24, wherein the articulation means includes a control wire extending between the distal end of the catheter tube and an actuator supported by the handle housing, the actuator being movable between first and second positions, the distal end of the catheter tube being deflected when the actuator is moved from the first to the second position.

27. The balloon catheter of claim 25, further comprising a second lumen extending from the handle housing and through the catheter body, the second lumen providing a passageway for the control wire.

28. The balloon catheter of claim 27, wherein the actuator comprises a lever pivotally mounted on the handle.

29. The balloon catheter of claim 27, wherein the actuator comprises a member slidably mounted on the handle.

* * * * *

UNITED STATES PATENT AND TRADEMARK OFFICE
CERTIFICATE OF CORRECTION

PATENT NO. : 5,344,397

DATED : September 6, 1994

INVENTOR(S) : Malcolm D. Heaven and Hira V. Thapliyal

It is certified that error appears in the above—identified patent and that said Letters Patent is hereby corrected as shown below:

Column 2, line 41, "The control wire can comprise" should read
--The control wire actuator can comprise--.

Column 3, line 46, "a manually repressible button" should read
--a manually depressible button--.

Column 4, line 4, "such as about 7 min." should read
--such as about 7 mm.--.

Column 5, line 31, "A manually repressible push-button" should read
--A manually depressible push-button--.

Column 7, line 12, "claim 5," should read
--claim 10--.

Column 7, line 20, "claim 5," should read
--claim 10--.

UNITED STATES PATENT AND TRADEMARK OFFICE
CERTIFICATE OF CORRECTION

PATENT NO. : 5,344,397

DATED : September 6, 1994

INVENTOR(S) : Malcolm D. Heaven and Hira V. Thapliyal

It is certified that error appears in the above-indentified patent and that said Letters Patent is hereby corrected as shown below:

Column 7, line 34, "positioned adjacent distal end" should read --positioned adjacent a distal end--.

Signed and Sealed this

Seventh Day of February, 1995

Attest:

BRUCE LEHMAN

*Attesting Officer*    Commissioner of Patents and Trademarks